(12) United States Patent
Damren et al.

(10) Patent No.: US 10,519,409 B2
(45) Date of Patent: Dec. 31, 2019

(54) SHAFT-MOUNTED FLUID TRANSFER ASSEMBLY FOR A DISPOSABLE BIOREACTOR

(71) Applicant: GE HEALTHCARE BIO-SCIENCES CORP., Marlborough, MA (US)

(72) Inventors: Richard Lee Damren, Marlborough, MA (US); Colin R. Tuohey, Marlborough, MA (US)

(73) Assignee: GE Healthcare Bio-Sciences Corp., Marlborough, MA (US)

( * ) Notice: Subject to any disclaimer, the term of this patent is extended or adjusted under 35 U.S.C. 154(b) by 223 days.

(21) Appl. No.: 15/534,633

(22) PCT Filed: Dec. 22, 2015

(86) PCT No.: PCT/EP2015/080957
§ 371 (c)(1),
(2) Date: Jun. 9, 2017

(87) PCT Pub. No.: WO2016/107788
PCT Pub. Date: Jul. 7, 2016

(65) Prior Publication Data
US 2017/0362555 A1    Dec. 21, 2017

Related U.S. Application Data

(60) Provisional application No. 62/098,494, filed on Dec. 31, 2014.

(51) Int. Cl.
*C12M 1/04* (2006.01)
*C12M 1/00* (2006.01)
(Continued)

(52) U.S. Cl.
CPC ........ *C12M 23/14* (2013.01); *B01F 3/04539* (2013.01); *B01F 7/00383* (2013.01);
(Continued)

(58) Field of Classification Search
CPC ....... C12M 23/14; C12M 23/28; C12M 27/04
See application file for complete search history.

(56) References Cited

U.S. PATENT DOCUMENTS

| | | |
|---|---|---|
| 4,019,962 A | 4/1977 | Allen et al. |
| 5,897,012 A | 4/1999 | Sortwell |
| (Continued) | | |

FOREIGN PATENT DOCUMENTS

| | | |
|---|---|---|
| GB | 2189773 A | 11/1987 |
| WO | 2007/034271 A1 | 3/2007 |
| (Continued) | | |

OTHER PUBLICATIONS

PCT International Search Report and Written Opinion for PCT Application No. PCT/EP2015/080957 dated Mar. 29, 2016 (9 pages).

(Continued)

*Primary Examiner* — Jonathan M Hurst
(74) *Attorney, Agent, or Firm* — Eversheds Sutherland (US) LLP

(57) ABSTRACT

A fluid transfer assembly for single use bioreactors includes a fluid transfer housing that can be mounted to the impeller shaft using a bearing that places the fluid transfer assembly directly below the lowest impeller but allows the impeller shaft to spin inside independently of the fluid transfer assembly. A fluid conduit connects the fluid transfer housing to a port in the single use bag wall which allows fluids to be introduced into the sparger and which also helps prevent the fluid transfer assembly from rotating with the impeller shaft.

24 Claims, 16 Drawing Sheets

(51) Int. Cl.
   *B01F 7/00* (2006.01)
   *B01F 15/00* (2006.01)
   *B01F 3/04* (2006.01)

(52) U.S. Cl.
   CPC ...... *B01F 7/00633* (2013.01); *B01F 7/00641* (2013.01); *B01F 15/0085* (2013.01); *B01F 15/00707* (2013.01); *C12M 1/04* (2013.01); *C12M 23/28* (2013.01); *C12M 27/04* (2013.01); *C12M 29/06* (2013.01); *B01F 2003/04553* (2013.01); *B01F 2003/04673* (2013.01)

(56) References Cited

U.S. PATENT DOCUMENTS

| | | |
|---|---|---|
| 6,029,839 A | 2/2000 | Mansouri |
| 6,461,500 B1 | 10/2002 | Hoage et al. |
| 10,260,036 B2 * | 4/2019 | Shor ................ C12M 33/14 |
| 2006/0092761 A1 | 5/2006 | Terentiev |
| 2010/0178685 A1 * | 7/2010 | Kloss ................ B01F 3/04539 435/243 |
| 2011/0013473 A1 | 1/2011 | Ludwig et al. |
| 2016/0333300 A1 | 11/2016 | Kronenberg |

FOREIGN PATENT DOCUMENTS

| | | |
|---|---|---|
| WO | 2013/040161 A1 | 3/2013 |
| WO | 2013/171340 A2 | 11/2013 |

OTHER PUBLICATIONS

Database WPI, XP002755326 of JPS5645752 dated Apr. 25, 1981.
European Search Report for EP Application No. 19160102.0 dated May 28, 2019 (10 pages).

\* cited by examiner

SHAFT-MOUNTED FLUID TRANSFER ASSEMBLY FOR A DISPOSABLE BIOREACTOR

CROSS REFERENCE TO RELATED APPLICATIONS

This application claims the priority benefit of PCT/EP2015/080957 filed on Dec. 22, 2015 which claims priority benefit of U.S. Provisional Patent Application No. 62/098,494 filed Dec. 31, 2014. The entire contents of which are hereby incorporated by reference herein.

FIELD OF THE INVENTION

The present invention relates to the field of disposable bioreactors. More specifically, the present invention relates to a fluid transfer assembly for a disposable bioreactor.

BACKGROUND OF THE INVENTION

In microbial bioreactors, sparge gas needs to be applied in close proximity to the lowest impeller, preferably directly under the lowest Rushton impeller. When using single use bioreactor bags reliably getting a bottom tethered sparger mechanism close to the impeller without actually hitting the impeller is difficult. Using a bottom tethered impeller also makes fabrication/assembly of a single use bag more difficult.

The art has seen the provision of a bioreactor sparger that is concentric about, but separate from, the impeller shaft where the sparger was a series of tubes with holed drilled in them that were tethered to the bottom of the single use bioreactor bag just below the lowest Rushton impeller. This design suffers from fabrication difficulties and that the sparger structure added an element of rigidity to the bottom of the single use bioreactor bag. Having the sparger tethered to the bag meant that its position with respect to the Rushton impeller could vary.

This sparger was a system of semi-rigid plastic tubes (with small holes drilled in them) in a semi-circular shape with an additional cross bar. The sparger was parallel to the vessel bottom and the impeller shaft passed vertically through the two cross bars spanning the semi-circular tubes. The sparger was located above the impeller core which contains the coupling magnets and below the lowest Rushton impeller on the impeller shaft.

It is known that microbial cells have protective cell walls, and tend to clump together when grown in a bioreactor. Microbial cell cultures thus require high speed, shearing impellers to break apart the clumps of cells; and require large amounts of air. Microbial cultures grow and multiply approximately twenty to forty (20-40) times faster than do mammalian cell cultures. Hence, the rates of oxygen consumption in a microbial cell fermentation culture are about 20 to 40 times greater than are those rates in a mammalian culture process.

In order to sustain growth in a microbial culture, a bioreactor for use in microbial systems must be capable of supplying oxygen to the culture faster than a bioreactor used for mammalian cells, and must be capable of breaking up clumps of cells.

The art has also seen perfusion devices which are located within the bioreactor for drawing fluid out from the bioreactor cavity.

The art lacks a shaft-mounted fluid transfer device which can act to provide either sparge gas or a feed fluid below the shaft-mounted impeller blades but above the bottom surface of a flexible or disposable bioreactor container. There is also a need for a fluid transfer device for a bioreactor which may be utilized along the length of the impeller shaft, below each impeller hub mounted on the shaft. Additionally, the art lacks a shaft-mounted fluid transfer device which can alternatively function as a perfusion device for a bioreactor.

SUMMARY OF THE INVENTION

The present invention provides a shaft-mounted fluid transfer assembly for use with a bioreactor. Additionally, the present invention provides a fluid transfer housing which may be rotatably-mounted to a shaft in a bioreactor. The present invention also provides an impeller assembly for a bioreactor which incorporates a fluid transfer housing or a fluid transfer assembly as shown and described. Alternatively still, the present invention provides a bioreactor incorporating a fluid transfer housing rotatably mounted to an impeller shaft, such that the impeller shaft extends through the impeller shaft passageway of the housing body. The bioreactors incorporating the present invention are desirably single-use or disposable in design.

The present invention further contemplates providing multiple fluid transfer housings of the present invention rotatably mounted on an impeller shaft, such as a second fluid transfer housing mounted opposite an impeller hub from a first fluid transfer housing, each fluid transfer housings are desirably provided as part of two distinct fluid transfer assemblies of the present invention. Alternatively again, the present invention provides an impeller shaft having two distinct impeller hubs each supporting impeller blades with a fluid transfer housing of the present invention provided under each of the impeller hubs. Bioreactors incorporating the fluid transfer housings of the present invention include an elongate conduit extending between an input port of the fluid transfer housing and a port affixed to a wall of the bioreactor so as to allow fluids to pass between the outside of the bioreactor and the container cavity by passing through the fluid transfer housing of the present invention.

DETAILED DESCRIPTION OF THE PREFERRED EMBODIMENTS

Figure 1:
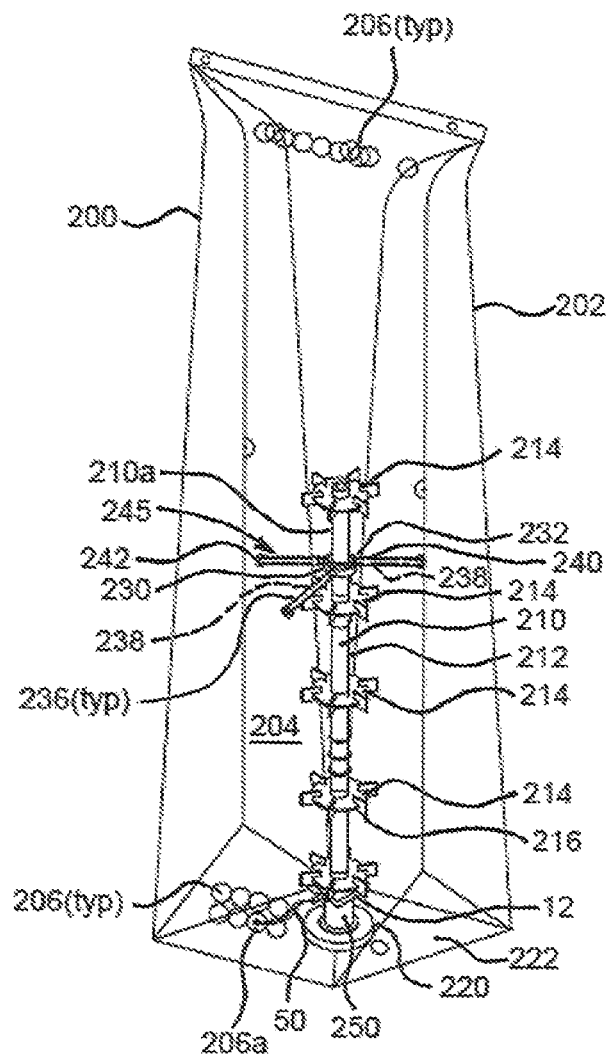
FIG. 1 depicts a disposable bioreactor incorporating a shaft-mounted fluid transfer assembly of the present invention.

The present invention provides a fluid transfer assembly having a fluid transfer housing rotatably mounted to an impeller shaft of a bioreactor. The bioreactor may be a single-use or disposable bioreactor formed with a flexible container or bag in which a biological samples or materials may be generated. The single-use bioreactor desirably is positioned within a rigid housing that allows access to the container as well as means for rotating the impeller therein. The fluid transfer housing may provide gases or liquids required for a bioreactor process. Alternatively, the fluid transfer housing my withdraw fluid from the bioreactor. The fluid transfer housing is designed to be mounted directly to the shaft by a rolling element bearing that will enable the shaft to rotate at high speeds and for prolonged periods of time while the fluid transfer housing is tethered to a sidewall of the bioreactor, desirably by a fluid transfer conduit which spans from the sidewall to the fluid transfer housing. The fluid transfer conduit is designed to provide liquids or gases to the fluid transfer housing or to withdraw fluid from the bioreactor through the fluid transfer housing. The fluid transfer housing of the present invention is thus suitable for providing sparge gas or feed fluids as well as acting as a perfusion device.

The fluid transfer assembly of the present invention desirably includes a housing rotatably mounted on the impeller shaft, where the housing defines an internal passageway leading to one or more outlet ports defined by the housing to be in fluid communication with the internal passageway. The housing also defines a port for connecting to a fluid conduit extending between the housing and a port provided on the wall of a bioreactor. The present invention contemplates that the fluid transfer assembly of the present invention may be utilized on an impeller shaft and may be provided in the cavity of a bioreactor with the second end of the conduit connected to a port provided on the wall of a bioreactor. Fluid, either in liquid or gaseous form, may be provided through the port on the flexible wall, through the conduit and internal passageway and out of the one or more outlet ports of the housing. Thus, in addition to its suitability as a gas sparger, the present invention is suitable for adding liquids to the bioreactor directly under the impeller where mixing would be maximized. An example would be the addition of liquid feeds during a bioreactor run.

The fluid transfer assembly of the present invention also allows for more than one fluid transfer assembly to be installed along the length of an impeller shaft if so desired. Depending on the needs of a bioreaction process, one or more fluid transfer assemblies of the present invention may thus provide feed fluids and/or sparge gas, while one or more fluid transfer assemblies may also draw fluid from the container cavity.

The fluid transfer housing may further support a porous surface, mesh screen, or membrane across the outlet ports. Additionally, the fluid transfer assembly of the instant invention may direct fluid from the bioreactor through the one or more outlet ports into the internal passageway and through the conduit and the port mounted on the wall of the conduit. The pore size of the porous surface is desirably from about 2 microns to about 10 millimeters, or from about 5 microns to about 3 millimeters. The porous surface associated may be configured for allowing the passage of an inlet gas stream and controlling gas bubble size and distribution prior to addition of the inlet gas stream to the interior of the single chamber is also adapted for use as a particulate separation device.

The fluid transfer assembly of the present invention is desirably mounted to a shaft in a bioreactor, desirably a disposable or single-use bioreactor container or bag. The bioreactor may provide any volume as a reaction chamber, and has been demonstrated in a 500 liter vessel that is specifically designed to handle the process demand of microbial fermentation. These cells have a short doubling time and as a result of the rapid growth they consume more oxygen and generate more heat than the typical mammalian cell applications for which bioreactors were originally developed. The system attributes to support this application has a large agitator motor and multiple impellers mounted to a long shaft capable of delivering the required power to the fluid. This long shaft has a feature to stabilize the top of the shaft through a mechanism that rigidly connects the tank wall to the impeller inside the bag. The agitator is bottom driven through a magnetic coupling with the drive head. The high gas flows necessitate large filters and a condenser system to preserve the life of the exhaust filters and reduce the volume loss in the reactor. The heat transfer surface area is maximized with a jacketed door that results in both high heat transfer surface area and makes bag installation easier.

The fluid transfer assembly of the present invention is suitable for use as a sparger for single use microbial bioreactors as it can be mounted to the impeller shaft directly below the lowest Rushton impeller but includes a bearing that allows the impeller shaft to spin inside the sparger. A sparge gas line consisting of silicone tubing connects the sparger to a port in the single use bag wall which allows sparge gas to be introduced into the sparger and which also keeps the sparger from rotating with the impeller shaft.

As a sparger, the fluid transfer assembly of the present invention provides a system which allows very vigorous agitation to disperse air bubbles to maximize the surface area, thereby increasing absorption of air bubbles; the impeller repeatedly breaking up larger bubbles and breaking up clumps of cell. The fluid transfer assembly of the present invention is rotatably mounted on an impeller shaft so as to allow independent rotation of the impeller shaft while the fluid delivery system is tethered to the flexible container of a bioreactor. The impeller shaft also supports impeller blades mounted to rotate with the shaft such that the vigorous mixing of the solution by the impeller tends to draw up the oxygen through the cell suspension in order to supply oxygen at a rapid rate to the cells.

The fluid transfer assembly of the present invention may thus provide a sparger which is separate from the bottom of the bag and placed on a bearing that is concentric about the impeller shaft. The present invention thus provides a fluid transfer housing providing sparge gas or feed fluid to be located directly below the Rushton impeller—and since its position is determined by the impeller shaft itself it is always exactly where it should be with regards to the Rushton impeller for maximum effect. This design also lends itself to allowing additional spargers to be located at different positions along the impeller shaft if the need for additional sparge capacity is required.

Figure 2:
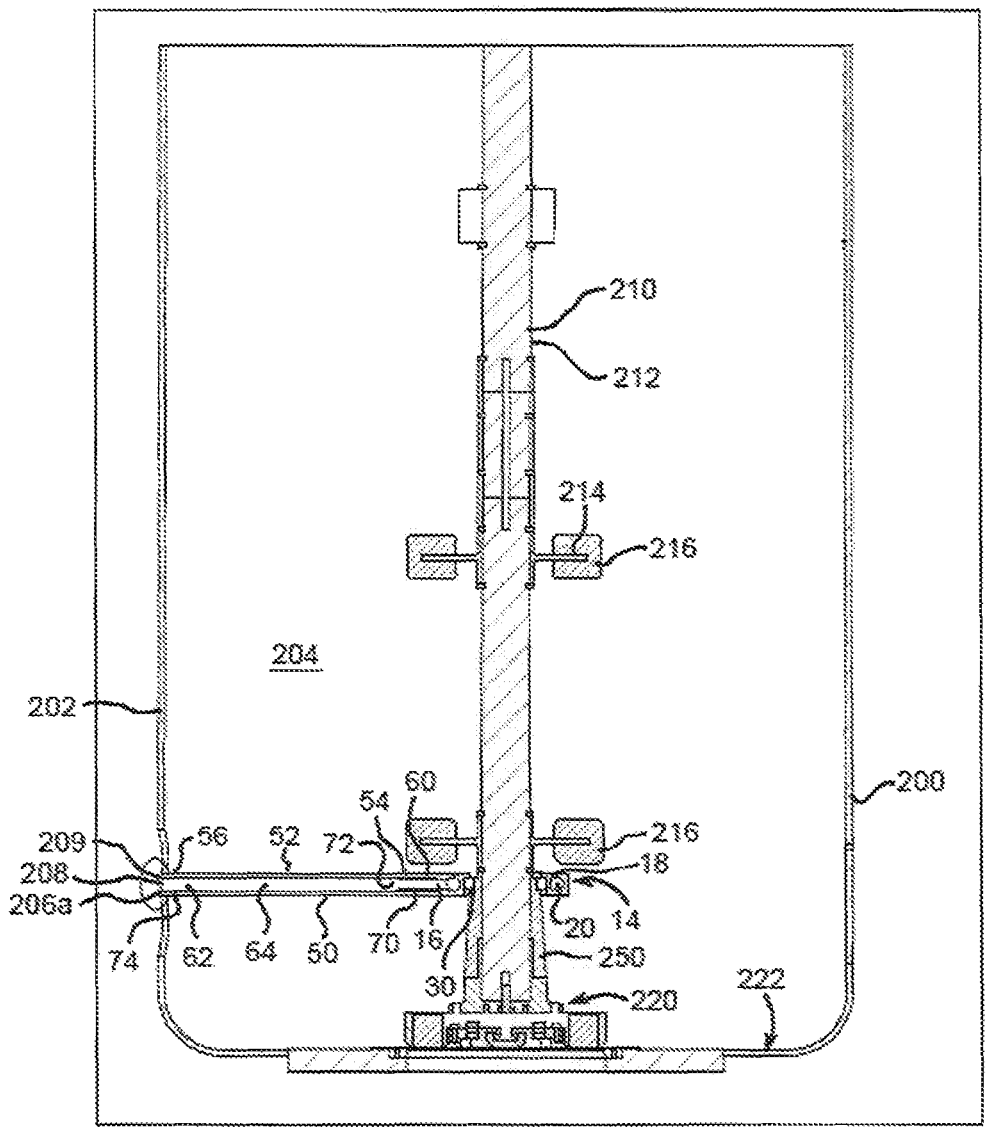
FIG. 2 depicts a cross-sectional view of a shaft-mounted fluid transfer assembly of the present invention.
Figure 3:
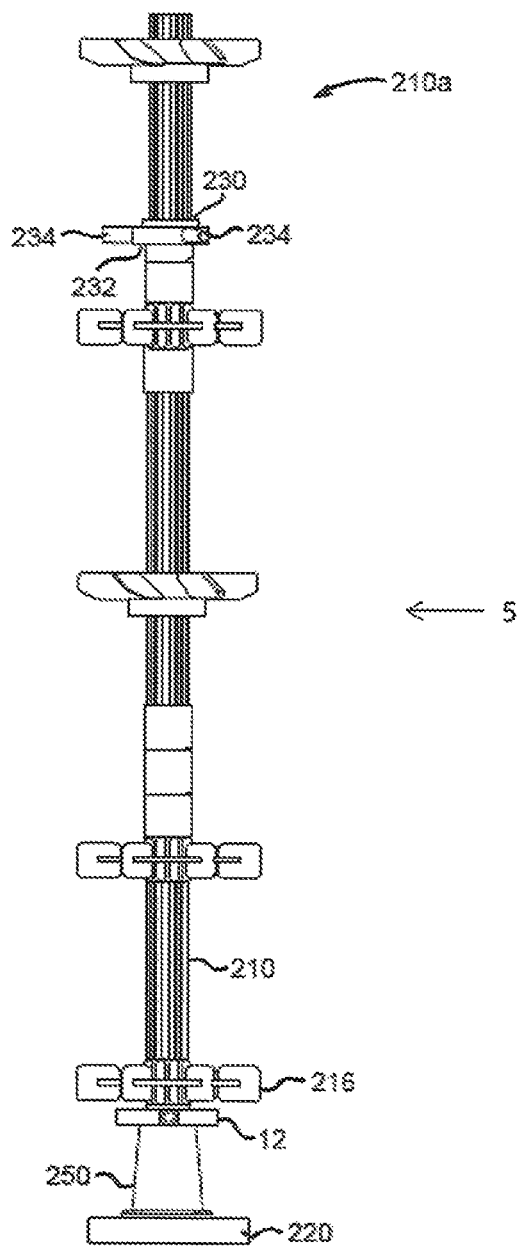
FIG. 3 depicts a fluted impeller shaft having a fluid transfer housing of the present invention mounted thereon.
Figure 4:
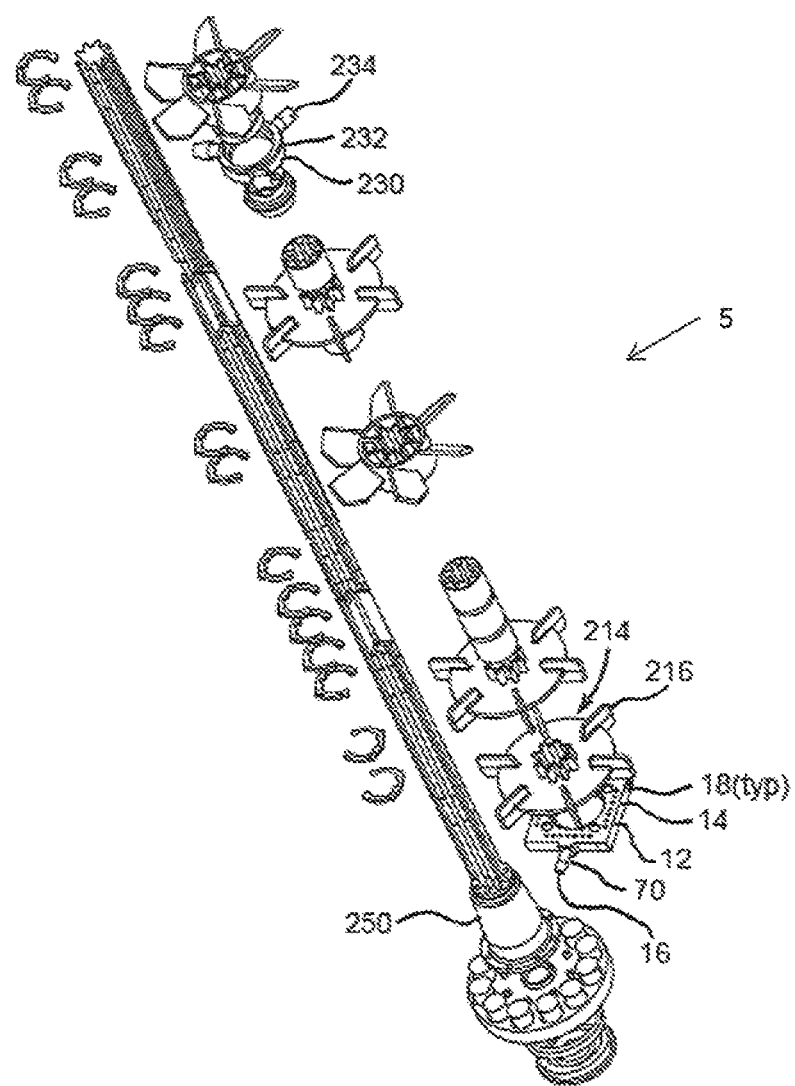
FIG. 4 depicts an exploded view of the fluted impeller shaft of FIG. 3.
Figure 5:
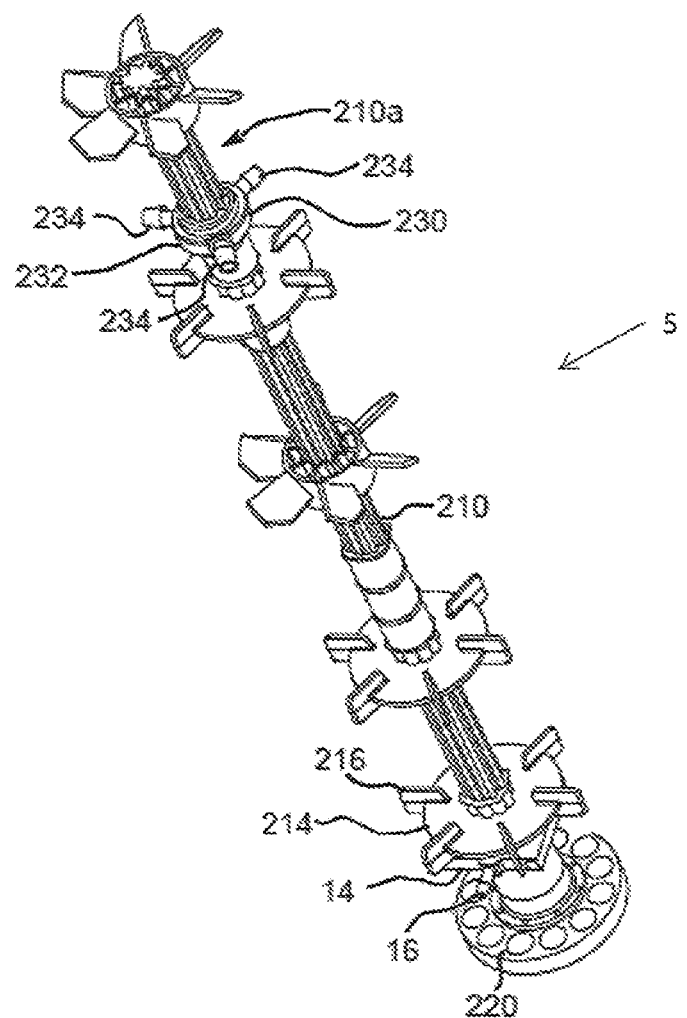
FIG. 5 depicts an oblique view of the fluted impeller shaft of FIG. 3.
Figure 6A:
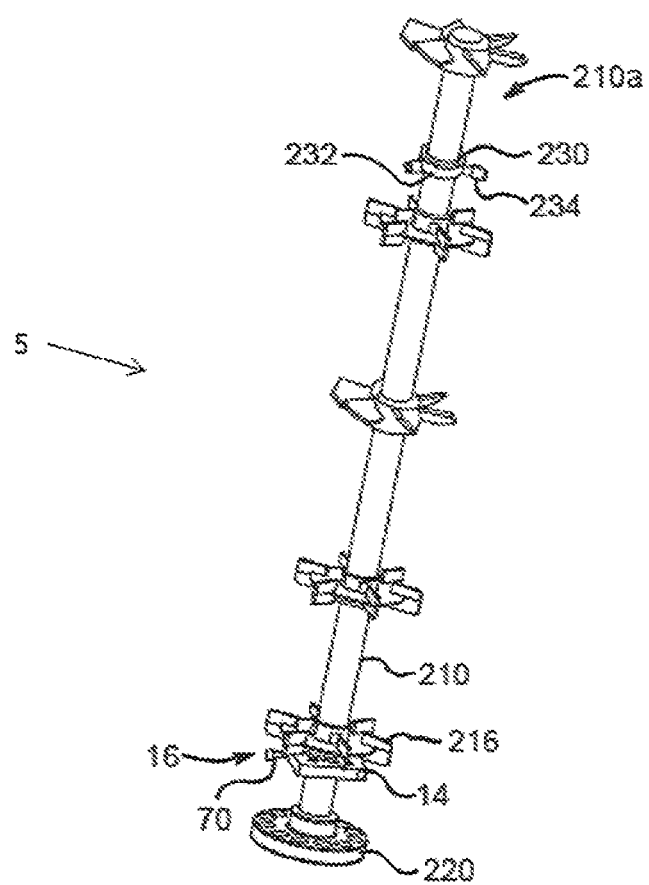
FIG. 6A-C depicts a solid impeller shaft having a fluid transfer housing of the present invention mounted thereon.
Figure 6B:
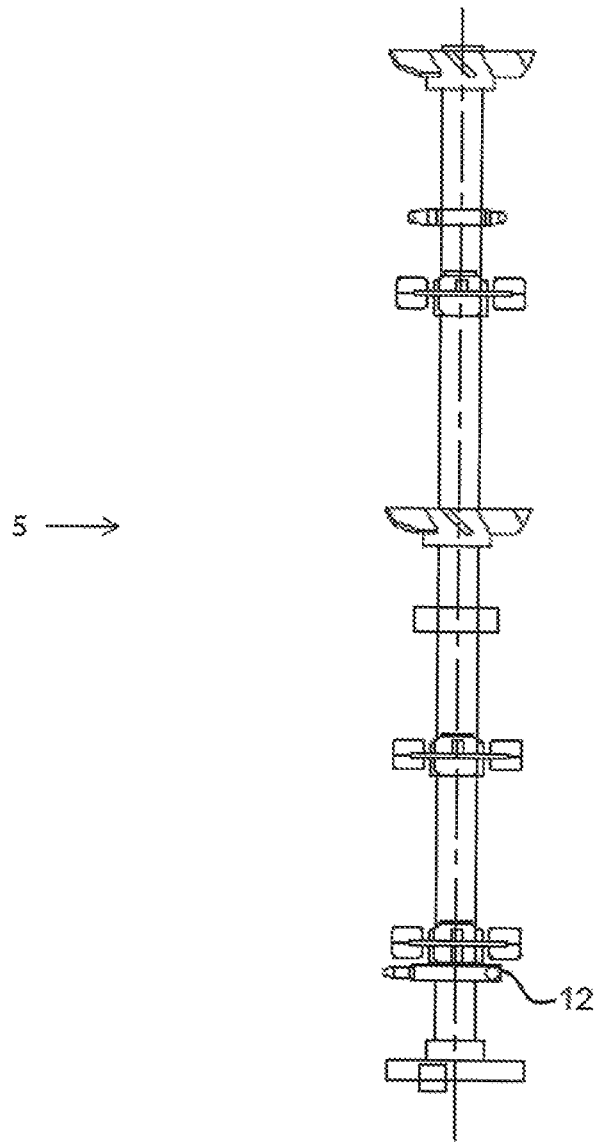
Figure 6C:
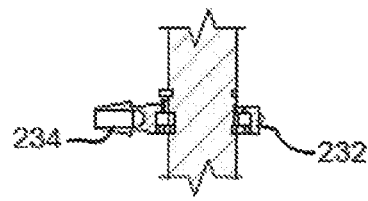
Figure 6C:
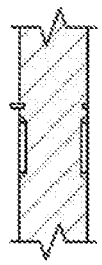
Figure 6C:
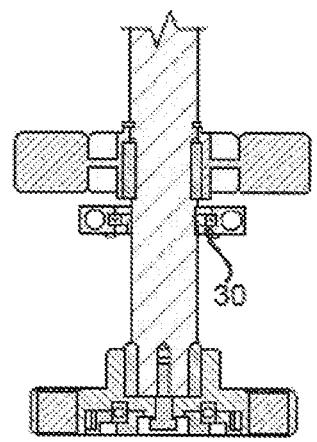
Figure 7:
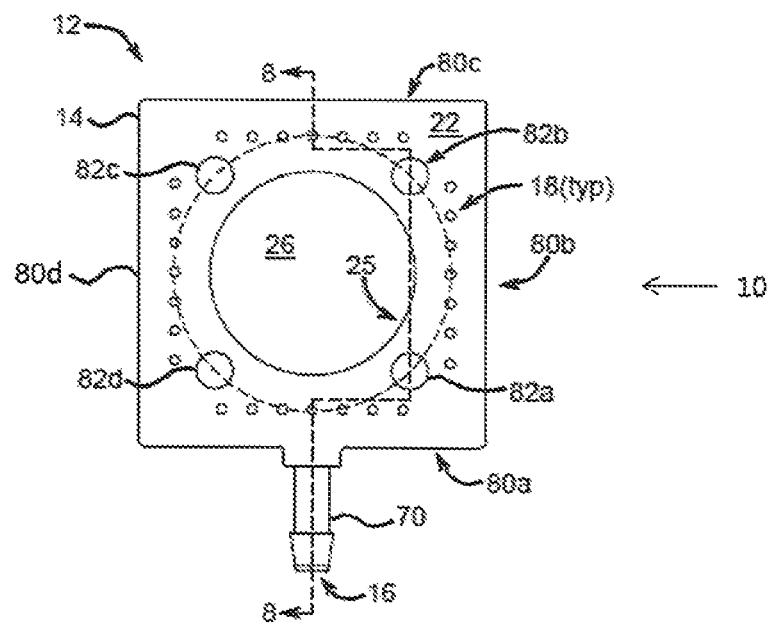
FIG. 7 depicts a fluid transfer housing of the present invention.
Figure 8:
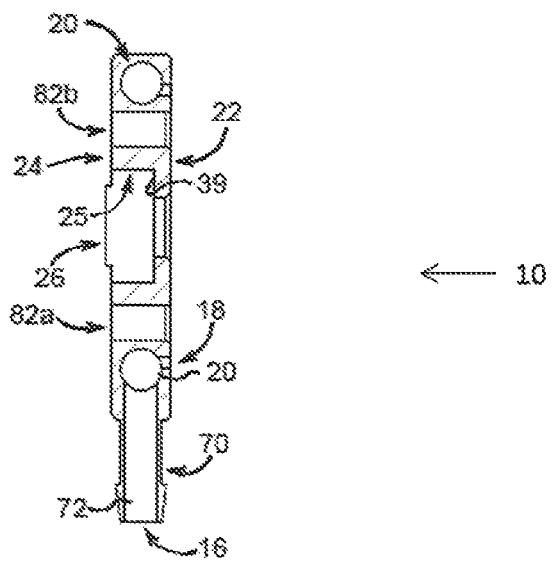
FIG. 8 depicts a cross-sectional view of the fluid transfer housing of FIG. 7 taken through line 8-8.
Figure 9:
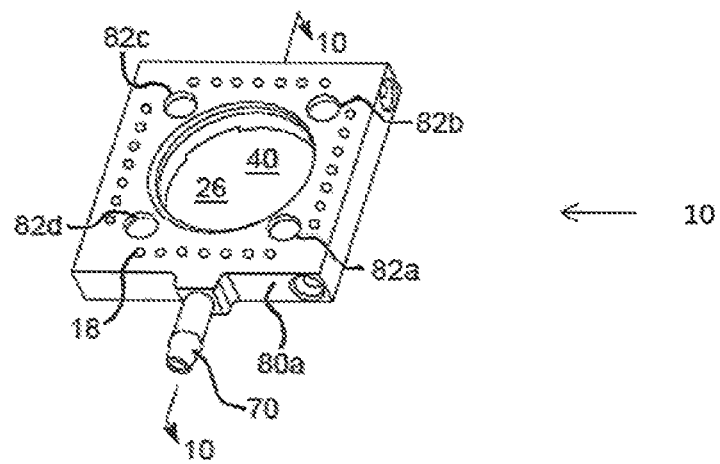
FIG. 9 depicts an oblique view of the fluid transfer housing of FIG. 7.

With reference to FIGS. 1-18, the present invention provides a fluid transfer assembly 10 for a disposable bioreactor 200. Bioreactor 200 desirably includes a flexible container wall 202 which defines an elongate container cavity 204. Container wall 202 typically includes a plurality of fluid ports 206 for the introduction or removal of fluids into container cavity 204. Bioreactor 200 furthermore supports an elongate rotatable impeller shaft 210 having an elongate shaft body 212 which supports one or more impeller hubs 214 affixed thereto so as to rotate with impeller shaft 210. Each impeller hub 214 includes a number of impeller blades 216 projecting radially therefrom. Shaft 210 includes a rotatable shaft base 220 mounted to a bottom surface 222 of container wall 202. Shaft base 220 includes a number of magnets spaced about shaft 210. The magnets may be magnetically coupled to a driving magnet provided outside of bioreactor 200 such that as the driving magnet rotates its magnets, the magnetically coupled magnets of shaft 210 will also rotate, causing shaft 210 to also rotate. Such a magnetically-coupled drive system allows for shaft 210 to be maintained completely within container cavity 204 and thus maintain a clean environment in container cavity 204. As shown in FIG. 2, bioreactor 200 desirably fits within a stainless steel bioreactor housing 205. Housing 205 desirably allows access to all of the ports 206 of container 202 and accommodates a magnetic drive motor which causes shaft 210 to rotate within cavity 204. The present invention is also contemplated to work with shafts which extend through the container wall, as the present invention is not dependent on the particular drive system for causing shaft 210 to rotate.

Shaft 210 also supports a holding collar 230 adjacent the free end 210a thereof. Holding collar 230 is used to support the free end 210a of shaft 210 and thus maintain the position and orientation of shaft 210 within cavity 204. Holding collar 230 is positioned about shaft 210 and includes an annular collar body 232 defining receptacles 234. Each receptacle 234 receives a first end 240 of a support rod 236 therein. Support rods 236 include an elongate body 238 extending between opposed first and second ends 240 and 242, respectively. Second end 242 of rods 236 extend out to be coextensive with container wall 202. Desirably, bag 210 provides an elongate flexible sleeve 245 extending from container wall 202 to the receptacle 234 for each rod 236. Sleeve 245 is affixed at each end to collar 230 and to a port or receptacle affixed to wall 202 (and through which the second end 240 of rod 236 is inserted) so as to minimize the effect that the material of shaft 236 has on the reactions taking place within cavity 204. As with the type of shaft drive mechanism, the manner by which the free end, is steadied within cavity 204 is not important to the present invention as the fluid transfer device of the present invention operates independently of the manner by which the shaft is held steady.

The present invention contemplates all of the fluid-contacting components used to form bioreactor 200 are formed from materials which are suitable and compatible with the desired reaction to take place within cavity 204. Additionally, the materials used to form bioreactor 200 are desirably formed from materials suitable for single-use, or disposable, bioreactors, including but not limited to suitable polymers and ceramics.

With particular reference to FIGS. 7-10 and 12-13, fluid transfer assembly 10 includes a fluid transfer housing 12 having a housing body 14 defining an input port 16, at least one outlet port 18, and an elongate housing passageway 20 extending in fluid communication therebetween. Housing body 14 includes opposed major surfaces 22 and 24 and further defines an open shaft passageway 26 extending between, and opening on, major surfaces 22 and 24. Impeller assembly 5 further includes impeller shaft 210 and at least one impeller hub 214 with a plurality of impeller blades 216. Fluid transfer assembly 10 includes a rolling element bearing 30 affixed within shaft passageway 26. Rolling element bearing 30 includes concentric inner and outer bearing races 32 and 34, respectively, which hold a bearing cage 36 and a plurality of rolling elements 38 therebetween. Rolling element bearing 30 can be a roller bearing or a ball bearing, with rollers or balls respectively constituting the rolling elements 38. Outer bearing race 34 is affixed to housing body 14 and inner bearing race 32 includes an inner surface 35 defining a shaft aperture 40 such that inner race 32 is affixable to impeller shaft 210 so that shaft 210 may rotate independently of housing body 14. A rolling element bearing 30 tested with the present invention was obtained from Xing Lun Bearings Group Limited of Ningbo, China. Inner and outer races 32 and 34, as well as the balls 38, may be formed from a ceramic material which is suitable for bioreactor applications. The present invention contemplates that inner surface 35 conforms to the outer surface of shaft 210. Alternatively, as shown in FIGS. 15-18, inner surface 35 conforms to extend about outer surface 256 of an adaptor 250. Adaptor 250 includes an adaptor body 252 having an outer surface 254 and an inner surface 256 defining a through passageway 258 designed to receive and engage the outer surface of shaft 210. Thus if shaft 210 has a fluted design as shown, eg, in FIGS. 3-5, inner surface 256 desirably provides a mating undulating surface for engaging the fluted shape. Alternatively, if shaft 210 has a cylindrical outer surface as shown, eg, in FIG. 6, inner surface 35 may have a mating cylindrical shape. Adaptor body 252 is designed to rotate with shaft 210 so that inner race 32, being affixed to outer surface 254, is said to be affixed to shaft 210. As outer race 34 is affixed to housing body 14, relative rotation between inner and outer race 32 and 34 is enabled by rolling elements 38.

FIGS. 15-18 depict one embodiment for affixing outer race 34 to housing body 14 and inner race 32 to adaptor 250. Shaft body includes first and second transversely-extending annular rims 260 and 262 separated by an annular wall 264. A second annular wall 266 extends from second rim 262. Annular rim 262 and annular wall 266 thus extend radially-inwardly of rim 260 and wall 264. A first locking ring 270 is positioned about annular wall 266 so as to force or hold inner race 32 against second annular rim 262. Locking ring 270 and adaptor 250 may be formed of a similar polymer. A second locking ring 272 is positioned inside of annular wall 25 of housing body 14 so as to force or hold outer race 34 against a transversely-extending annular rim 39 of housing body 14. Inner race 32 is thus held stationary with respect to adaptor 250 and shaft 210 while outer race 34 is held stationary with respect to housing body 14. Shaft 210 is thus able to rotate independently of housing body 14 in accordance with the present invention.

Desirably, housing body 14 defines a plurality of outlet ports 18 in fluid communication with housing passageway 20 where both housing passageway 20 and outlet ports 18 extend about shaft passageway 26. The present invention contemplates that outlet ports 18 may have different shapes or sizes from each other, so as to provide a desired uniformity to fluid flow from housing 12. For example, the outlet ports closer to input port 16 may be smaller in dimension or shaped differently than the outlet ports positioned opposite housing body 14 from inlet port 16. Outlet ports 18 are desirably positioned directly below impeller blades 216 which rotate with shaft 210.

Fluid transfer assembly 10 further includes an elongate fluid conduit 50 extending from inlet port 206a affixed to bioreactor wall 202 to input port 16 of housing body 14. Fluid conduit 50 includes an elongate tubular body 52 extending between opposed first and second open ends 54 and 56, respectively. First open end 54 defines a first conduit aperture 60, second open end defines a second conduit aperture 62 and tubular body defines an elongate conduit passageway 64 extending in fluid communication therebetween. Fluid conduit 50 thus places outlet port 16 of housing body 14 in open fluid communication with fluid port 206a of bioreactor wall 202. Thus a liquid or gas is able to transit from a source outside of bioreactor 200, through conduit 50, through input port 16 into housing passageway 20 and out through outlet ports 18 into container cavity 204. Similarly, liquid may be drawn through ports 18 into housing passageway 20 and out input port 16 through conduit 50 to a receptacle located outside of bioreactor 200. Desirably, housing body includes an elongate hollow stem 70 projecting from housing body 14 and defining inlet port 16 and an open elongate port passageway 72 in open fluid communication with housing passageway 20. Similarly, port 206a includes an elongate hollow port stem 74 projecting from container wall 202 and defining a through port (open aperture) 208 and an open elongate port passageway 209. First end 52 of conduit 50 is affixed about stem 70, and second end 54 is connected to port stem 74, by conventional means including but not limited to an annular two-piece clip or a cable tie.

The present invention contemplates that conduit 50 may also serve as a tether which holds housing body 14 relatively still while shaft 210 rotates within cavity 204. It is further contemplates that additional or alternative means may be employed to tether housing body 14 so as to not rotate with shaft 210, including for purposes of illustration and not of limitation a separate tether anchored to a stationary member of bioreactor 200 within cavity 204 or an elongate sleeve anchored over conduit 50 but which is able to bear a majority of the load imparted by housing body 14 on conduit 50 as shaft 210 rotates. However, in internal testing, a conduit 50 anchored to a port 206a positioned radially-outward from housing 14 has demonstrated an ability to withstand high speed rotation of shaft 210 for extended periods of time.

Housing body 14 includes opposed first and second planar major surfaces 22 and 24, respectively, and a perimetrical side wall 80 extending between said first and second major surfaces 22 and 24. Desirably, input port 16 is defined by side wall 80 and stem 70 projects from side wall 80. Desirably, first major surface 22 defines the outlet ports 18 to be in fluid communication with said housing passageway. First major surface 22 thereby desirably defines outlet ports 18 arrayed about shaft aperture 40 although one or more outlet ports may also be defined by sidewall 80.

Figure 10:
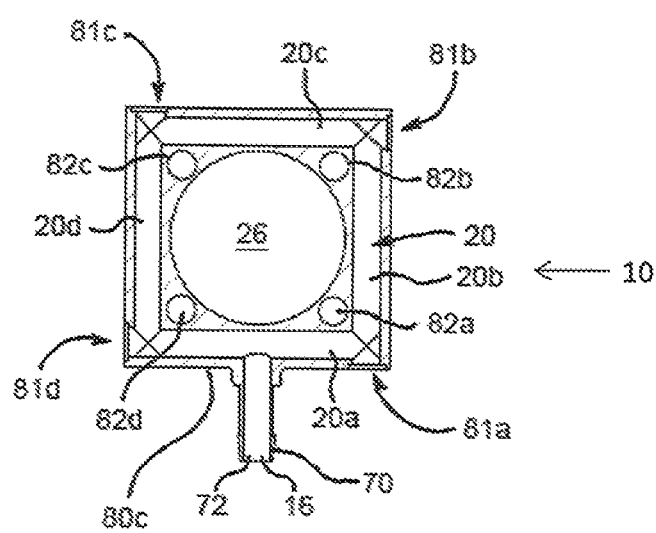
FIG. 10 depicts a cross-sectional view of the fluid transfer housing of FIG. 7, taken through the line 10-10 of FIG. 9.
Figure 11:
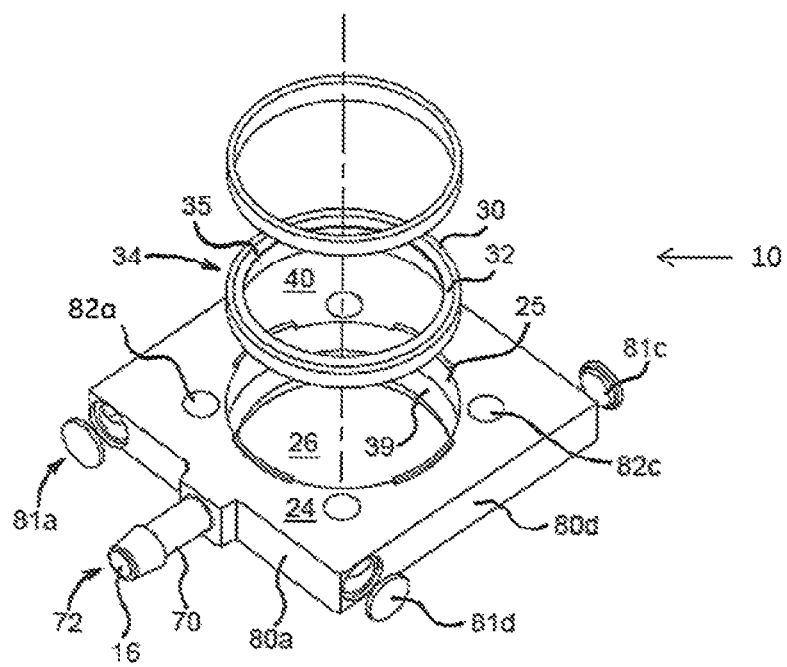
FIG. 11 depicts a oblique exploded view of a the bottom of a fluid transfer housing of the present invention depicting the assembly of the bearing to the fluid transfer housing.
Figure 12:
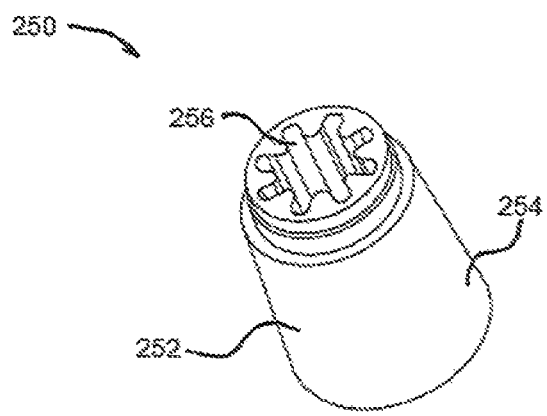
FIG. 12 depicts an oblique view of the shaft adapter used to mount the fluid transfer assembly of the present invention to a fluted shaft.
Figure 13:
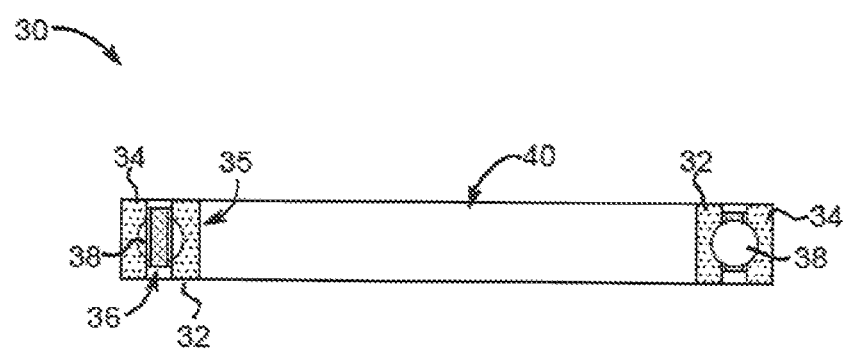
FIG. 13 depicts a cross-sectional view of a bearing used with the fluid transfer housing.
Figure 14:
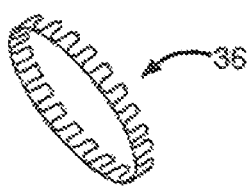
FIG. 14 depicts an oblique view of the bearing cage which holds the ball bearing between the inner and outer races of the bearing of FIG. 13.
Figure 15:
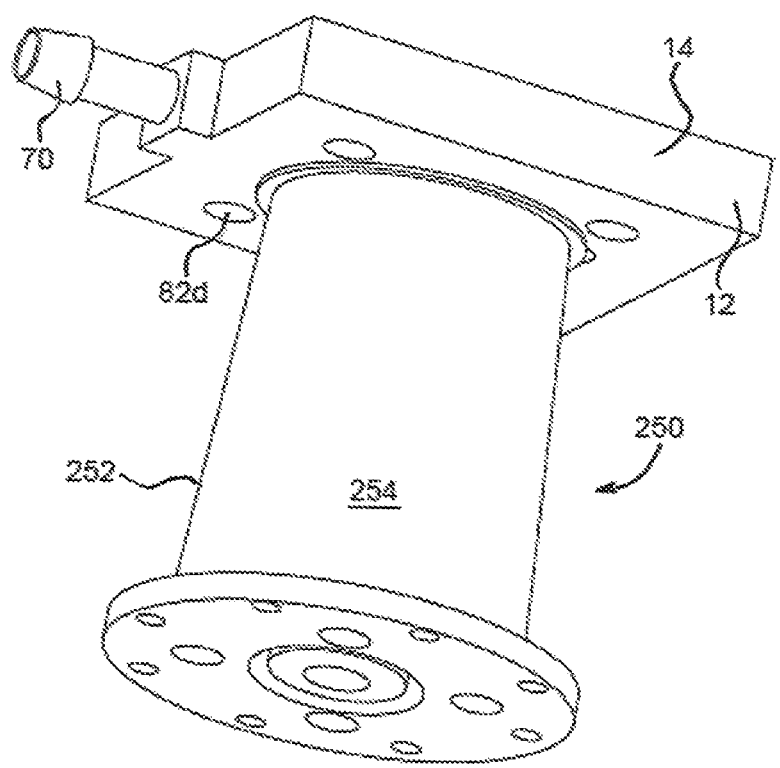
FIG. 15 depicts a fluid transfer housing of the present invention mounted to a shaft adapter.
Figure 16:
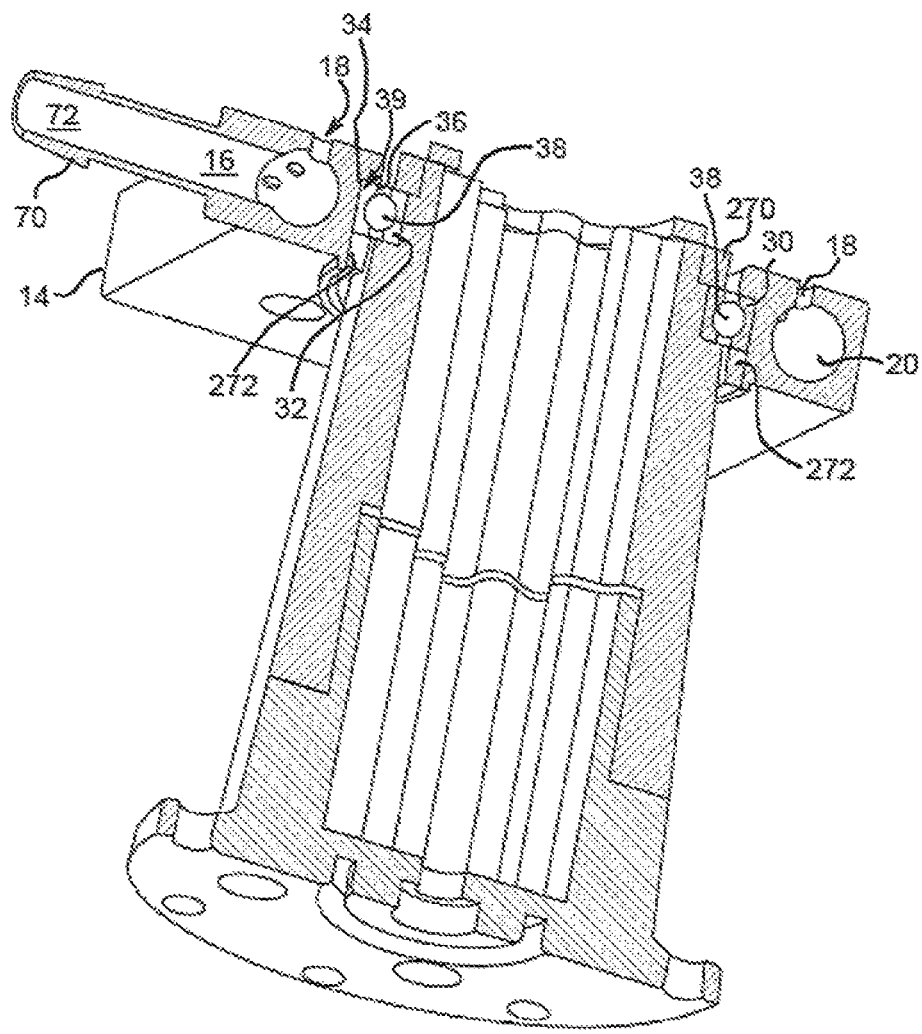
FIG. 16 depicts a cross-sectional view of the fluid transfer housing mounted to a shaft adapter taken through line 16-16 of FIG. 15.
Figure 17:
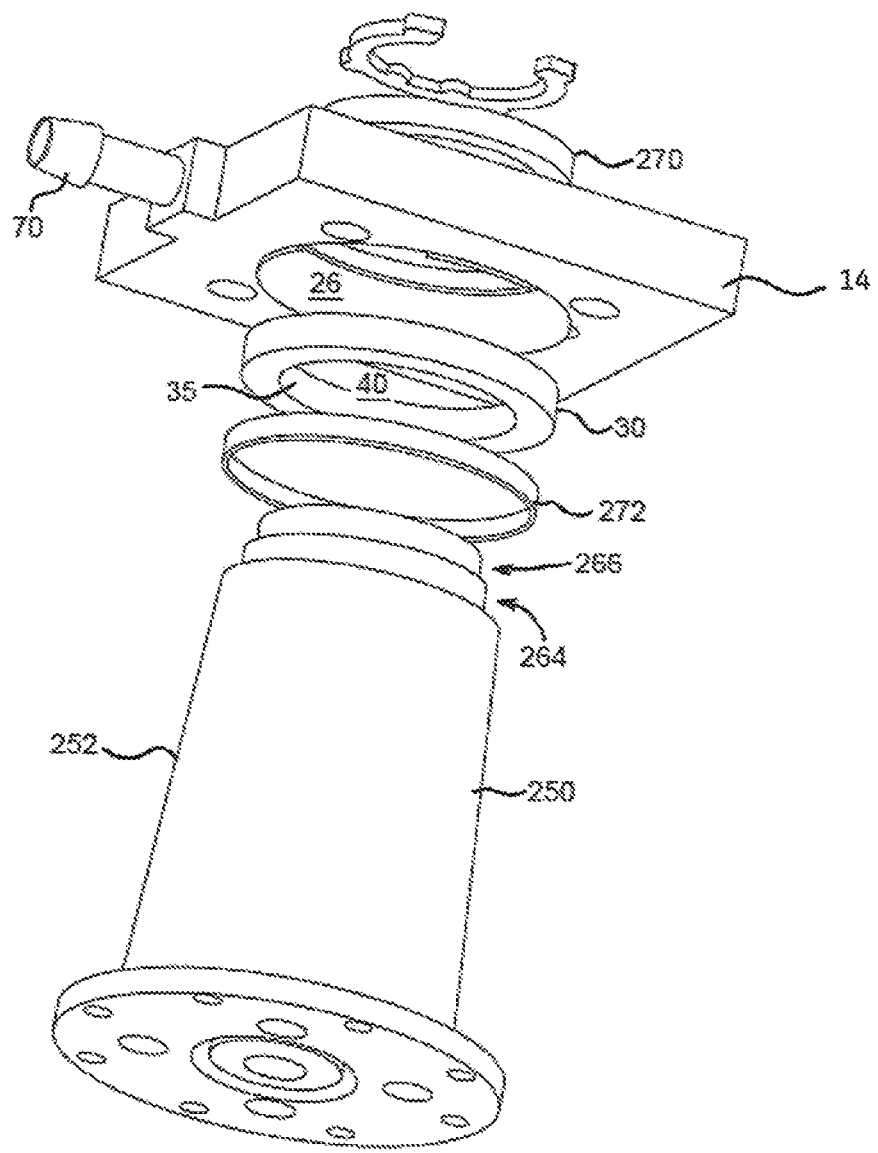
FIG. 17 depicts an exploded view of how a fluid transfer assembly retains the bearing and is mounted to a shaft.
Figure 18:
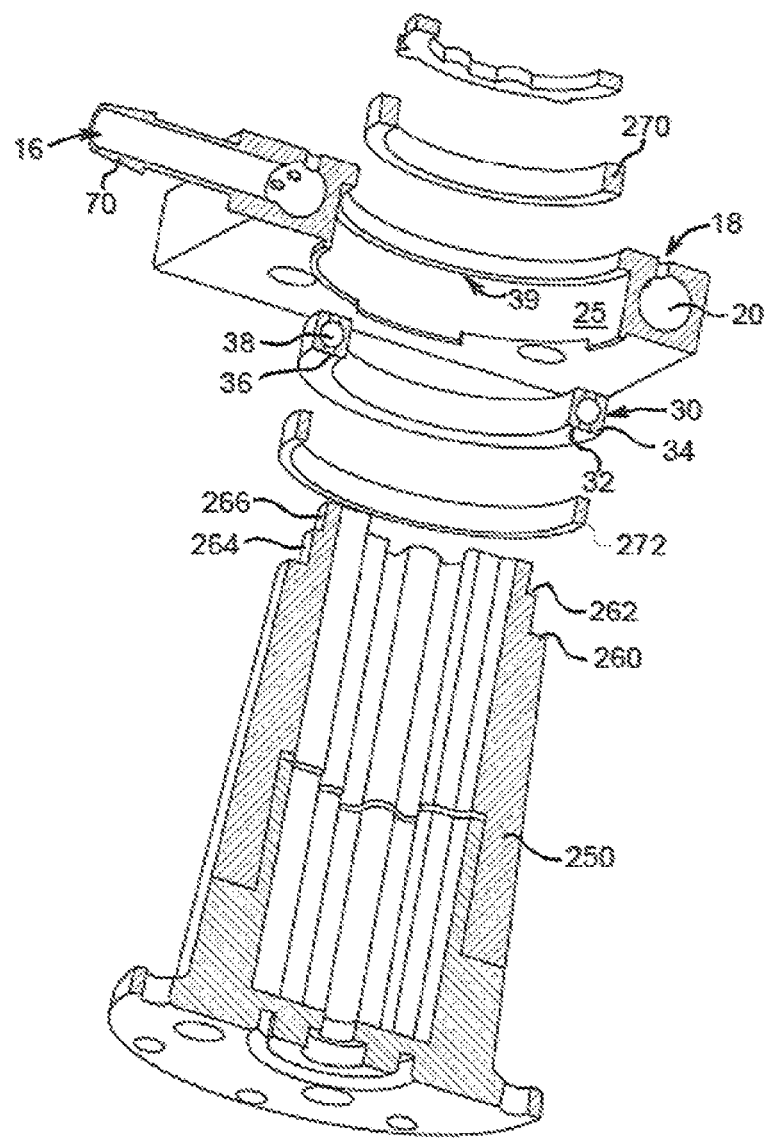
FIG. 18 depicts a cross-sectional exploded view of how a fluid transfer is mounted to a shaft.

In one embodiment of the present invention, housing passageway 20 is defined to extend along perimetrical side wall 80 and about shaft aperture 40. With particular reference to FIG. 10, housing passageway 20 may be formed having four linear segments 20a-d. Each of linear segments 20a-d may be formed by machining (or subtractive manufacturing) the segment from one of sidewall segments 80a-d, respectively. Each segment 20a-d is sealed by a sidewall plug 81a-d affixed along sidewall segments 80a-d. Alternatively, housing body may be formed from two overlying planar components which define passageway 20 therebetween and either together or individually define input port 16 and/or outlet ports 18. It is further contemplated by the instant invention that housing passageway 20 need not be annular about shaft aperture 40, and may alternatively be blocked at some point about shaft aperture 40 so as to approximate a "C" shape.

Housing body 14 further defines at least one open reactor passageway 82 extending therethrough, adjacent to shaft passageway 40, in a direction substantially parallel to shaft 210. Reactor passageways 82a-d are provided to allow fluid flow therethrough due the action of the impeller blades and thereby reduce the obstruction posed by housing body 14 on the desired mixing flow within cavity 204. While housing body 14 is shown having a generally square shape (as defined by perimetrical wall 80), the present invention contemplates that housing body 14 may alternatively have a general shape selected from ring-shaped and polygonal-shaped. Additionally, while major surfaces 22 and 24 have been shown and described as planar, the present invention contemplates that each could have opposing arcuate shapes or be otherwise non-planar. Similarly, while perimetrical side wall 80 has been shown and described as having planar segments, these segments may alternatively have a shape selected from rounded cylindrical and polygonal cylindrical.

The present invention further contemplates that housing body 14 may additionally provide a porous member spanning each outlet port 18. The porous member may be a frit as is known in the sparger art or may alternatively be a porous membrane spanning each outlet port. Alternatively, a single porous membrane may be affixed within passageway 20 so as to span all of outlet ports 18. The pore size of the porous member is contemplated to be between about 2 micrometers to about 10 millimeters. Alternatively, the pore size of the porous member is from about 2 micrometers to about 3 millimeters. Alternatively still, the pore size of the porous member may be from about 5 micrometers to about 3 millimeters. The porous member may be adapted for providing smaller gas bubbles to the rotating impeller blades or may also be adapted for use as a particulate separation device such as when housing body is used for withdrawing fluid from cavity 204.

While the particular embodiment of the present invention has been shown and described, it will be apparent to those skilled in the art that changes and modifications may be made without departing from the teachings of the invention. For example, the particular shape of the fluid transfer housing, the shape of the internal passageway, and the shape and number of housing apertures may be modified without departing from the instant invention. The matter set forth in the foregoing description and accompanying figures is offered by way of illustration only and not as a limitation. The actual scope of the invention is intended to be defined in the following claims when viewed in their proper perspective based on the prior art.

What is claimed is:

1. A fluid transfer assembly for a disposable bioreactor comprising:
   a fluid transfer housing having a housing body defining an input port, at least one outlet port and an elongate housing passageway extending in fluid communication therebetween;
   said housing body further defining an open shaft passageway extending therethrough; and
   a rolling element bearing affixed within said shaft passageway, said rolling element bearing comprising concentric inner and outer bearing races and a plurality of rolling elements positioned between the inner and outer bearing races, the outer bearing race being affixed to the housing body and the inner bearing race including an inner surface defining a shaft aperture such that the inner race is affixable to an impeller shaft so that the shaft may rotate independently of said housing body.

2. The fluid transfer assembly of claim 1, further comprising a plurality of outlet ports in fluid communication with said housing passageway.

3. The fluid transfer assembly of claim 1, wherein said housing body includes opposed first and second planar major surfaces and a perimetrical side wall extending between said first and second major surfaces.

4. The fluid transfer assembly of claim 3, wherein said input port is defined by said perimetrical side wall of said housing.

5. The fluid transfer assembly of claim 3, wherein said first major surface of said housing body defines said at least one outlet port.

6. The fluid transfer assembly of claim 5, wherein said first major surface defines a plurality of outlet ports in fluid communication with said housing passageway.

7. The fluid transfer assembly of claim 3, wherein said housing passageway is defined to extend along the perimetrical side wall about said shaft aperture.

8. The fluid transfer assembly of claim 7, wherein said first major surface of said housing body defines a plurality of outlet ports in fluid communication with said housing passageway, wherein said plurality of outlet ports are arrayed about said shaft aperture.

9. The fluid transfer assembly of claim 3, further comprising a porous member spanning said outlet aperture.

10. The fluid transfer assembly of claim 9, wherein the pore size of the porous member is from about 2 micrometers to about 10 millimeters.

11. The fluid transfer assembly of claim 9, wherein the pore size of the porous member is from about 2 micrometers to about 3 millimeters.

12. The fluid transfer assembly of claim 9, wherein the pore size of the porous member is from about 5 micrometers to about 3 millimeters.

13. The fluid transfer assembly of claim 9, wherein the porous member associated with the outlet port is also adapted for use as a particulate separation device.

14. The fluid transfer assembly of claim 1, wherein said inlet port is further defined by an elongate port stem projecting from said housing body, said port stem defining an open elongate port passageway in open fluid communication with said housing passageway.

15. The fluid transfer assembly of claim 1, wherein said housing body further defines at least one open reactor passageway through said housing body, said reactor passageway positioned adjacent to said shaft passageway.

16. The fluid transfer assembly of claim 1, wherein said housing body has a general shape selected from ring-shaped, square-shaped, and polygonal-shaped.

17. The fluid transfer assembly of claim 3, wherein said perimetrical side wall has a shape selected from rounded cylindrical and polygonal cylindrical.

18. The fluid transfer assembly of claim 1, further comprising an elongate fluid conduit extending from said input port of said fluid transfer housing, said fluid conduit having opposed first and second ends and an elongate tubular conduit body extending therebetween, said first end of said fluid conduit defining a first conduit aperture, said second end of said fluid conduit defining a second conduit aperture, and said conduit body defining an elongate conduit passageway extending in open fluid communication therebetween, said fluid conduit for placing said outlet port of said fluid transfer housing in open fluid communication with a fluid port of a container wall, such that fluid may be provided between the fluid port of the container wall and a bioreactor cavity defined by the container through said fluid transfer housing.

19. An impeller assembly for a disposable bioreactor, said impeller assembly comprising:
   an elongate impeller shaft having opposed first and second ends and an elongate shaft body extending therebetween;
   at least one impeller hub comprising a plurality of impeller blades, said hub mounted to said impeller shaft;
   the fluid transfer assembly of claim 1, the fluid transfer housing of said fluid transfer assembly being rotatably mounted to said impeller shaft, such that said impeller shaft extends through said shaft passageway of said housing body.

20. The impeller assembly of claim 19, wherein the inner race of said bearing is affixed to said impeller shaft.

21. The impeller assembly of claim 19, comprising a second fluid transfer assembly of any one of claims 1-18, the fluid transfer housing of said second fluid transfer assembly being rotatably mounted to said impeller shaft, such that said impeller shaft extends through said shaft passageway of said housing body, said second fluid transfer assembly mounted opposite said at least one impeller hub from said first fluid transfer assembly.

22. The impeller assembly of claim 19, further comprising a second impeller hub comprising a plurality of impeller blades, said second impeller hub mounted to said impeller shaft at a location opposite said second fluid transfer housing from said at least one impeller hub.

23. A disposable bioreactor comprising:
   a flexible bioreactor container having a flexible container wall defining a bioreactor cavity;
   the impeller assembly of claim 19 provided in said bioreactor cavity;
   a fluid port mounted to said container wall, said fluid port defining an open aperture through said container wall;
   an elongate fluid conduit extending from said fluid port of said bioreactor wall to said input port of said fluid transfer housing, said fluid conduit having opposed first and second ends and an elongate tubular conduit body extending therebetween, said first end of said fluid conduit defining a first conduit aperture, said second end of said fluid conduit defining a second conduit aperture, and said conduit body defining an elongate conduit passageway extending in open fluid communication therebetween, said fluid conduit placing said outlet port of said fluid transfer housing in open fluid communication with said fluid port of said container wall, such that fluid may be provided between said fluid port of said container wall and said bioreactor cavity through said fluid transfer housing.

24. The fluid transfer assembly of claim 1, wherein the plurality of rolling elements are balls or rollers.

* * * * *